US008765134B2

(12) United States Patent
Risk (10) Patent No.: US 8,765,134 B2
(45) Date of Patent: *Jul. 1, 2014

(54) METHODS FOR TREATING CHRONIC OBSTRUCTIVE PULMONARY DISEASE

(76) Inventor: Clifford G. Risk, Marlborough, MA (US)

( * ) Notice: Subject to any disclaimer, the term of this patent is extended or adjusted under 35 U.S.C. 154(b) by 0 days.
This patent is subject to a terminal disclaimer.

(21) Appl. No.: 13/305,222

(22) Filed: Nov. 28, 2011

(65) Prior Publication Data

US 2012/0070431 A1 Mar. 22, 2012

Related U.S. Application Data

(63) Continuation of application No. 11/917,575, filed as application No. PCT/US2006/025654 on Jun. 30, 2006, now Pat. No. 8,080,249.

(60) Provisional application No. 60/695,675, filed on Jun. 30, 2005.

(51) Int. Cl.
*A61K 39/395* (2006.01)
*C07K 16/42* (2006.01)

(52) U.S. Cl.
CPC ....... *C07K 16/4291* (2013.01); *A61K 39/39566* (2013.01); *C07K 2317/76* (2013.01); *Y10S 424/805* (2013.01); *Y10S 424/81* (2013.01)
USPC ..................... 424/153.1; 424/133.1; 424/805; 424/810; 514/1.7

(58) Field of Classification Search
None
See application file for complete search history.

(56) References Cited

U.S. PATENT DOCUMENTS

| 5,994,511 | A | * | 11/1999 | Lowman et al. | 530/387.3 |
| 8,080,249 | B2 | * | 12/2011 | Risk | 424/153.1 |
| 2005/0026881 | A1 | * | 2/2005 | Robinson et al. | 514/170 |
| 2005/0158303 | A1 | * | 7/2005 | Liu et al. | 424/131.1 |
| 2005/0261208 | A1 | * | 11/2005 | Robinson et al. | 514/25 |

FOREIGN PATENT DOCUMENTS

| WO | WO 9304173 | | 3/1993 |
| WO | WO 9967293 A1 | * | 12/1999 |

OTHER PUBLICATIONS

Risk et al. Chest, vol. 126, No. 4, Oct. 2004 supplement, p. 839s.*
Risk et al. Chest, vol. 128, No. 4, Oct. 2005 supplement, p. 243s.*
Itabashi et al., Respiration. 1990;57(6):384-8.*
Barnes, "Chronic Obstructive Pulmonary Disease," The N Engl J Med, 343:269-280 (2000).
Bleeker, "Similarities and Differences in Asthma and COPD. The Dutch Hypothesis," Chest 2004:126:93S-95S.
Bousquet et al., "Predicting Response to Omalizumab, an Anti-IgE Antibody, in Patients with Allergic Asthma," Chest, 125:1378-1386 (2004).
Burrows et al., "Association of Asthma with Serum IgE Levels and Skin-Test Reactivity to Allergens," The New Enge J Med, 320:271-277 (1989).
Busse et al., "Omalizumab, Anti-E Recombinant Humanized Monoclonal Antibody for the Treatment of Severe Allergic Asthma," J Allergy Clin Immunal, 184-190 (2001).
Celedon et al., Eur. Resp. J. 14:1009-1014 (1999).
Dakhama et al., "The Role of Virus-Specific Immunoglobulin E in Airway Hyperresponsiveness," Am J Respir Crit Care Med, 171:952-959 (2004).
Djukanovic et al., "Effects of Treatment with Anti-Immunoglobulin E Antibody Omalizumab on Airway Inflammation in Allergic Asthma," Am J Respir Crit Care Med, 170:583-593 (2004).
Elias,. "The Relationship Between Asthma and COPD. Lessons from Transgenic Mice," Chest, 126:111S-116S (2004).
Fabbri et al., "Similarities and Differences Between Exacerbations of Asthma and Chronic Obstructive Pulmonary Disease," Thorax, 53:803-808 (1998).
Greenberger PA, "Allergic Bronchopulmonary Aspergillosis," J Allergy Clin Immunol, 110:685-92 (2002).
Groneberg et al., Respiratory Research, 5(1):18:1-16 (Nov. 2, 2004).
Hargreave et al., "Induced Sputum, Eosinophilic Bronchitis, and Chronic Obstructive Pulmonary Disease," Am J Respir Crit Care Med, 160:S53-S57 (1999).
Holgate et a., "Efficacy of Omalizumab Anti-Immunoglobulin E antibody, in Patients with allergic Asthma at High Risk of Severe Asthma-Related Morbidity and Mortality," Current Medical Research and Opinions, 17(4):233-240 (2001).
Itabashi et al., Respiration, 57:384-8 (1990).
Lapparre et al., "Dissociation of Lung Function and Airway Inflammation in Chronic Obstructive Disease," Am J Respir Crit Care Med, 170:499-504 (2004).
Lewis et al. Chest, 119:105-114 (2001).
Milgrom et al., "Treatments of Allergic Asthma with Monoclonal Anti IgE Antibody," The N Engl J Med, 341:1966-1973 (1999).
Mitsunobu et al., "Influence of Long-Term Cigarette Smoking on Immunoglobulin E-Mediated Allergy, Pulmonary Function, and High Resolution Computed Tomography Lung Densitometry in Elderly Patients with Asthma," Clin Exp Allergy, 34:59-64 (2004).
Postma et al., "Rationale for the Dutch Hypothesis," Chest 2004, 126:965-04S.
Rohde et al., "Increased IgE-Antibodies to Staphylococcus aureus Enterotoxins in Patients with COPD," Respiratory Medicine, 98:858-64 (2004).
Sciurba, "Physiologic Similarities and Differences Between Asthma and COPD," Chest, 126:117S-124S (2004).
Soler et al., "The Anti-IgE Antibody Omalizumab Reduces Exacerbations and Steroid Requirement in Allergic asthmatics," Eur Resp J, 18:254-261 (2001).

* cited by examiner

*Primary Examiner* — Michael Szperka
(74) *Attorney, Agent, or Firm* — McDermott Will & Emery LLP (57) ABSTRACT

The present invention provides methods of treating a mammal having chronic obstructive pulmonary disease (COPD), independent of both smoking status and asthma status, with a therapeutically effective amount of an anti-IgE moiety. In accordance with the invention, COPD patients with an elevated serum IgE level may benefit from the treatment methods disclosed. In certain instances, the methods of the disclosure have been found to be useful for the treatment of COPD patients regardless of their skin test results and/or in vitro reactivity to a perennial aeroallergen. Anti-IgE moieties, in accordance with the invention, include but are not limited to any IgG antibody that selectively binds to a given mammal immunoglobulin E (e.g., human immunoglobulin E) such as humanized anti-IgE, humanized murine monoclonal antibody, and/or Omalizumab.

7 Claims, 6 Drawing Sheets

Fig 1a. AVERAGE EXACERBATION RATE FOR EACH PATIENT

METHODS FOR TREATING CHRONIC OBSTRUCTIVE PULMONARY DISEASE

CROSS-REFERENCE TO RELATED APPLICATIONS

This application is a continuation of U.S. application Ser. No. 11/917,572 filed on Dec. 14, 2007, now U.S. Pat. No. 8,080,249, which is a national stage entry of PCT Application No. PCT/US2006/025654, filed Jun. 30, 2006, which claims priority to U.S. Provisional Patent Application Ser. No. 60/695,675, filed on Jun. 30, 2005, entitled "Novel Uses for IgE Antibodies." The contents of this application each of the above applications is incorporated herein by reference in its entirety as though fully set forth.

BACKGROUND OF THE INVENTION

1. Field of the Invention

The present invention relates to methods for the treatment of chronic obstructive pulmonary disease in patients with a comorbid component mediated by IgE antibody. More specifically, the present invention encompasses therapeutic modalities, and more particularly, relates to methods using known active entities for a novel indication.

2. Background of the Invention

Chronic Obstructive Pulmonary Disease

Chronic Obstructive Pulmonary Disease ("COPD") affects middle aged and elderly people, and is one of the leading causes of morbidity and mortality worldwide affecting as many as 14 million people in the United States. The World Health Organization predicts that by 2020 COPD will become the 5th most prevalent disease, and the 3rd most common cause of death (see P. J. Barnes, New Engl. Journ. Med. 343:269-279 (2000)). COPD is associated with major healthcare costs, largely due to expensive treatments such as long-term oxygen therapy and hospital admissions, as well as indirect costs including loss of working capacity. Recent epidemiological data suggests that the prevalence of the disease is underestimated.

COPD is characterized by a reduction in expiratory flow and slow forced emptying of the lungs which does not change markedly over several months Cigarette smoking (especially, long term cigarette smoking) is believed to be the leading cause of COPD (statistically, a smoker is 10 times more likely than a non-smoker to develop and die of COPD). Smoking cessation is the only measure that will slow the progression of COPD. Airflow obstruction in COPD is usually progressive in patients who continue to smoke eventually leading to disability and shortened survival time. Smoking cessation has been shown to slow the rate of decline to that of a non-smoker but the damage caused by smoking is irreversible.

Other etiological factors (e.g., airway hyper responsiveness or hypersensitivity, air pollution (e.g., sulfur dioxide and possibly second hand smoke), occupational chemicals (e.g., cadmium) and generally allergy) have been identified in the literature but are believed to account for only a minority of COPD cases. Other risk factors include: heredity, secondhand smoke, exposure to air pollution at work and in the environment, and a history of childhood respiratory infections.

COPD often entails: chronic coughing, frequent chest tightness, shortness of breath, an increased effort to breathe, increased mucus production, and frequent clearing of the throat. COPD is characterized by airflow obstruction caused by chronic bronchitis, emphysema, or both. Airway obstruction is incompletely reversible but some COPD patients do show some improvement in airway obstruction with treatment. Airway obstruction due to chronic and excessive secretion of abnormal airway mucus, inflammation, bronchospasm, and infection are believed to cause chronic bronchitis leading to chronic cough, mucus production or both. In emphysema instead, the elastin in the terminal bronchioles is destroyed leading to the collapse of the airway walls and inability to exhale. Emphysema is characterized by the destruction of the alveoli and the abnormal permanent enlargement of the air spaces distal to the terminal bronchioles, accompanied by destruction of their walls without apparent fibrosis (for a more detailed description see, *Harrison's Principles of Internal Medicine,* 12$^{th}$ Edition, Wilson, et al., eds., McGraw-Hill, Inc.).

Asthma by contrast, often has an onset in infancy, childhood or adolescence, though sometimes it may become manifest in the adult. It is often caused by exposure to an allergen, and is mediated by an immune system involving IgE. Patients typically present with acute shortness of breath, wheeze, cough, and congestion. Bronchial spasms of the airway are typically reversible with treatment, although in some cases there may be chronic bronchial obstruction due to thickening (remodeling) of the bronchial wall (for a more detailed description see, *Harrison's Principles of Internal Medicine,* 12$^{th}$ Edition, Wilson, et al., eds., McGraw-Hill, Inc.).

COPD: Therapies Available

Presently available treatments are merely ameliorative. They include avoidance of irritants such as tobacco smoke and breathing supplemental oxygen. In advanced cases of COPD, lung reduction surgery is sometimes performed, but it is not clear that it helps. There is very little currently available to arrest its progression and otherwise prevent its exacerbations, preserve lung function, and otherwise improve the quality of life of COPD patients. The arsenal of medications available to practitioners treating COPD patients have traditionally include: fast-acting, β2-agonists, anticholinergic bronchodilators, long-acting bronchodilators, antibiotics, and expectorants. Amongst the currently available treatments for COPD, short term benefits, but not long term effects, were found on its progression, from administration of anti-cholinergic drugs, adrenergic agonists, and oral steroids. Oral steroids are only recommended for acute exacerbations with long term use contributing to excess mortality and morbidity.

Short and long acting inhaled, adrenergic agonists are used to achieve bronchodilation and provide some symptomatic relief in COPD patients. This class of drugs has been shown to have no maintenance effect on the progression of the disease. Short acting adrenergic agonists improve symptoms in subjects with COPD, such as increasing exercise capacity and produce some degree of bronchodilation, and even an increase in lung function in some severe cases. The maximum effectiveness of the newer long acting inhaled, adrenergic agonists was found to be comparable to that of short acting, adrenergic agonists. Salmeterol was found to improve symptoms and quality of life, although only producing modest or no change in lung function. Notably, β-agonists can produce cardiovascular effects, such as altered pulse rate, blood pressure; and electrocardiogram results. Treatment of asthmatic and COPD patients with the bronchodilators ipratropium bromide or fenoterol was not superior to treatment on an asneeded basis, therefore indicating that they are not suitable for maintenance treatment. The combination of a β adrenergic agonist with an anti-cholinergic drug provides little additional bronchodilation compared with either drug alone. The addition of ipratropium to a standard dose of inhaled, β adrenergic agonists for about 90 days, however, produces some improvement in stable COPD patients over either drug alone. Overall, the occurrence of adverse effects with β adrenergic agonists, such as tremor and dysrhythmias, is more frequent than with anti-cholinergics. Thus, neither anti-cholinergic drugs nor, β-adrenergic agonists have an effect on all people with COPD; nor do the two agents combined.

Antibiotics are also often given at the first sign of a respiratory infection to prevent further damage and infection in diseased lungs. Expectorants help loosen and expel mucus secretions to from the airways, and may help make breathing easier. In addition, other medications may be prescribed to manage conditions associated with COPD. These may include: diuretics (which are given as therapy to avoid excess water retention associated with right-heart failure), digitalis (which strengthens the force of the heartbeat), and cough suppressants. This latter list of medications help alleviate symptoms associated with COPD but do not treat COPD.

Thus, there is very little currently available to alleviate symptoms of COPD, prevent exacerbations, preserve optimal lung function, and improve daily living activities and quality of life.

SUMMARY OF THE INVENTION

The present invention relates to the use of anti-IgE therapy for the treatment of COPD. More specifically, it has been found that anti-IgE therapy is useful for the treatment of patients with COPD, independent of both smoking status and asthma status. In addition, and as discussed hereinafter, anti-IgE modalities have been found useful for the treatment of COPD in patients with elevated IgE serum levels regardless of whether such patients have a positive skin test result or a positive in vitro reactivity test result.

The present invention provides methods of treating a mammal having COPD with a therapeutically effective amount of an anti-IgE moiety. Anti-IgE moieties contemplated include, but are not limited to any IgG antibody that selectively binds to a given mammal immunoglobulin E (e.g., human immunoglobulin E). In particular humanized anti-IgE antibodies are considered useful. Accordingly, in certain embodiments (including the non-limiting representative moieties exemplifying the advantages of the invention hereinafter) the humanized IgG antibody that selectively binds to human immunoglobulin E is a humanized murine monoclonal antibody. Specifically, anti-IgE moieties contemplated include Omalizumab.

COPD patients with an elevated serum IgE level may benefit from the treatment methods according to the invention. In certain instances, the methods of the invention have been found to be useful for the treatment of COPD patients regardless of their skin test results and/or in vitro reactivity to a perennial aeroallergen.

Other objects, features and advantages of the present invention will be set forth in the detailed description of the embodiments that follows, and in part will be apparent from the description or may be learned by practice of the invention. These objects and advantages of the invention will be realized and attained by the moieties, compositions and methods particularly pointed out in the written description and claims hereof.

BRIEF DESCRIPTION OF THE DRAWINGS

For a fuller understanding of the systems and processes of the present invention, reference is made to the following detailed description, which is to be taken with the accompanying drawings, wherein:

FIG. 1 is a graph showing representative clinical effects of treatment according to the invention with an anti-IgE moiety: Omalizumab as response of exacerbation rates.

FIG. 2 are regression scatter diagrams of treatment response against several independent characteristics; Decrease in exacerbation rate=exacerbation rate in the year prior to treatment minus the rate in the first year of treatment for each patient.

DETAILED DESCRIPTION

The models of allergic asthma and cigarette-induced COPD form the basis for understanding of the pathways of obstructive pulmonary disease. Our fundamental understanding of these two disorders is that they represent two distinct and very different diseases. The clinical differences in terms of symptoms, age of onset, clinical presentation, and treatment have been discussed in the Background of the Invention Section (supra). At the cellular level, these disorders are characterized by very different mechanisms. The IgE-mediated asthma typically involves white corpuscles that are eosinophils, and cellular mediators that include interlukin 4 and interlukin 5. By contrast, cigarette-induced COPD includes white corpuscles that are neutrophils, and cellular mediators including interlukin 8 and tumor necrosis factor.

In clinical practice, many of the patients often share characteristics of both disorders (the overlap syndrome) (see, Nonas S. A., *The Resp. Rep.* 1(1):11-17 (2005)). These shared characteristics include endogenous and exogenous factors that precipitate disease, cellular and cytokine profiles in sputum and serum, and pathologic findings (see, Seatti M., Stefano A., Maestrelli P., et al., *Am J Respir Crit. Care Med* 150:1646-1652 (1994); Fabbin L., Beghe B., Caramon G., et al., *Thorax* 53:803-808 (1998); Sciurba F., *Chest* 126: 1175-1245 (2004)). The role of immunoglobulin E (IgE)-mediated triggers is a case in point. They can be present in both asthmatic (Burrows B., Martinez F. D., Halonen M. N. Engl. J. Med. 320:271-277 (1989); Lapparre Therese S., Snoeck-Straland Jiska, Gosman Margot M. E., et al. Am. J. Respir. Crit. Care Med. 170:499-504 (2004) and COPD patients (Rohde G., Gevaert P., Holtappels G., et al. Repir. Med. 98:858-64 (2004); Greenberger P. A., J. Allergy Clin. Immunol. 110: 685-92 (2002).). Such IgE-mediated triggers may be subtle (Daklami A., Park J-W, Tauke C., et al. Am. J. Respir. Crit. Care Med. 171:952-959 (2004)) or even undefined (Humbert M., Durkam J. R., Ying S., et al. Am. J. Respir. Crit. Care Med. 154:1947-1504 (1996)).

While Omalizumab has been established as an effective treatment of the asthmatic patient with an IgE-allergy mediated response, heretofore it has not been suggested for the treatment of COPD. Because a considerable percentage of COPD patients have a strong primary cigarette history and in many cases there is documented secondary exposure to cigarette smoking, the present investigator evaluated the efficacy of Omalizumab for the treatment of COPD patients with a serum IgE≥30 IU ("elevated IgE") regardless of their smoking history and found that efficacy did not appear to be dependant on the presence or severity of a preceding cigarette history.

As evidenced by the data in the examples provided herein, it has been found that (a) patients with a severe obstructive pulmonary disease who have a qualifying elevated IgE level should not be excluded from consideration of anti-IgE therapy of the basis of their cigarette history alone; and (b) that the degree of skin rest reactivity does not appear to be a strong determinant of the response of anti-IgE treatment as evidenced by the results obtained with Omalizumab treatment. Notably, it was also found that the level of circulating IgE was also not a strong indication of response to Omalizumab treatment. It is postulated that while IgE at the cellular, mast cell, level is a critical determent of the asthmatic response, this may not be reflected in the level of circulating IgE.

Accordingly, the present invention provides methods for treating COPD by administering an effective amount of an anti-IgE moiety or a composition or a pharmaceutical composition comprising at least one anti-IgE moiety to a cell, tissue, organ, mammal in need of such modulation, treatment, alleviation, prevention, or reduction in symptoms, effects or mechanisms. In certain embodiments, the method entails the administration of a therapeutically effective amount of an anti-IgE moiety. Any anti-IgE moiety effective for the treatment according to the methods described herein which are presently described in the art is contemplated.

A moiety that inhibits the activity of IgE or an anti-IgE moiety/entity is one that contains at least one active entity capable of modulating (including reducing) IgE activity. IgE activity may be detected and possibly quantitated by the circulating levels of IgE, but can also be measured by activities associated with IgE function, such as binding to basophils, anaphylaxis, and binding to receptors such as Fc receptors.

Generally, entities that inhibit the activity of IgE may include, for example, anti-IgE antibodies, IgE receptors, anti-IgE receptor antibodies, variants of IgE antibodies, ligands for the IgE receptors, and fragments thereof. Variant IgE antibodies may have amino acid substitutions or deletions at one or more amino acid residues.

In certain embodiments of the invention the moiety capable of inhibiting the activity of IgE comprises an anti-IgE antibody. The anti IgE antibody may be a monoclonal antibody. The adjective "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The antibody may be a chimeric antibody. Monoclonal antibodies useful for the methods of the invention may also be isolated from phage antibody libraries using the techniques described in Clackson et al., *Nature*, 352:624-628 (1991) and Marks et al., *J. Mol. Biol.*, 222:581-597 (1991). The anti-IgE antibody may be a humanized murine antibody or a fully human antibody. The modifier "humanized" is used to designate non-human (e.g., murine) antibodies which are chimeric antibodies including immunoglobulins, immunoglobulin chains or fragments thereof (such as Fv, Fab, Fab', F(ab')2 or other antigen-binding subsequences of antibodies) which have been engineered to comprise only limited sequence derived from non-human immunoglobulin (i.e., have been engineered to favor human sequences). Considerable genetic modifications are routinely made in this context to further refine and optimize a given antibody performance. Generally, a humanized antibody optimally also will comprise at least a portion of an immunoglobulin constant region (Fc), typically that of a human immunoglobulin (see also, Jones et al., *Nature*, 321:522-525 (1986); Reichmann et al., Nature, 332:323-329 (1988); and Presta, *Curr. Op. Struct. Biol.*, 2:593-596 (1992)).

A representative anti-IgE antibody contemplated within the invention is Omalizumab, also designated as RhuMAb-E25 or E25. Another preferred anti-IgE antibody is designated in the literature as E26 (see infra). Various known anti-IgE antibodies are described in the prior art, and in greater detail in International applications WO 93/04173 and WO 99/01556. In particular WO 99/01556 specifically describes Omalizumab, also named E25, in FIG. 12, and in the sequences ID-No. 13-14. Antibody molecules comprising a E26 sequence are described in WO 99/01556 and are considered within the scope of suitable anti-IgE moieties as designated herein. The present invention also contemplates anti-IgE antibodies that bind soluble IgE but not IgE on the surface of B cells or basophils (see e.g., those disclosed in U.S. Pat. No. 5,449,760). Generally all antibodies binding to soluble IgE and inhibiting IgE activity by a variety of possible mechanisms are contemplated (e.g., by blocking the IgE receptor binding site, by blocking the antigen binding site and/or by simply sequestering IgE from circulation). Examples of anti-IgE antibodies and IgE-binding fragments derived from the anti-IgE antibodies which may be used according to the invention are described in U.S. Pat. No. 5,656,273 and U.S. Pat. No. 5,543,144.

Recombinant humanized anti-IgE monoclonal antibodies which have been extensively investigated include rhuMAb-E25 (Omalizumab, discussed in the previous paragraph) and CGP 56901 which block the binding of IgE to its high affinity receptor, thereby preventing the release of mediators (Fahy J. V. *Clin Exp Allergy* 30:16-21 (2000)). In several clinical trials, rhuMAb-E25 dramatically reduced serum levels of free IgE, attenuated both early and late phase responses to inhaled allergen, and significantly reduced asthma symptoms (see e.g., Milgram H., Fick R., Su J. Q., et al. *N. Engl. J. Med.* 341:1966-1973 (1999); Saker M., Matz J., Buhl R., et al. *Eur. Resp. J.* 18: 254-261 (2001); Busse W., Carren J., Lanier B. Q., et al. *J. Allergy Clin. Immunal.* 108-190 (2001); Holgate S., Bousqet J., Wenzel S., et al. *Current Medical Research and Opinions* 17:233-240 (2001); and Bousqet J., Wensel S., Holgate S. *Chest* 125:1378-1386 (2004)).

RhuMAb-E25 a.k.a. Omalizumab (commercialized under the mark XOLAIR®) is a recombinant humanized monoclonal antibody that blocks the high-affinity Fc receptor of immunoglobulin E (IgE). Omalizumab binds free serum IgE and surface IgE on B cell without binding to IgE on high or low affinity receptors present on effector cells thus, blocking the release of mediators of inflammation by inhibiting the association of IgE with mast cells and basophils. Clinical studies suggest that Omalizumab induces a rapid and sustained decrease in circulating IgE, and down-regulates the expression of the IgE binding domain receptor (FcεERI) leading to a reduced release of inflammatory mediators. The link between serum IgE levels and a positive skin test has led to the development of Omalizumab as a treatment of choice in many cases of asthma. Presently, Omalizumab is used to treat patients with moderate-persistent to severe-persistent asthma; patients must be older than 12 years, have a positive skin test to a perennial aeroallergen (e.g., dust mites, cats, dogs, and mold), and be symptomatic with inhaled corticosteroids. However, because the link between COPD and serum IgE levels remains poorly understood and attempts to use anti-IgE therapeutics for the treatment of COPD have not been pursued. In particular, attempts to treat COPD patients who are also skin test negative have not been pursued in the field.

The present invention relates to the unanticipated finding that individuals diagnosed with COPD surprisingly respond to treatment with Omalizumab. Even more surprisingly, it has been found that COPD patients who are also skin test negative and or have a negative result on the basis on in vitro testing for allergens and for whom Omalizumab would therefore not be indicated requiring either a positive skin test and or a positive in vitro reactivity test) respond to such treatment.

The terms "treatment" or "treat" or any permutation of the same as used herein include alleviation of one or more symptoms of the disorder, diminishment of the extent of the disorder, stabilization of the disorder, delay or slowing of disorder progression, amelioration or palliation of the disorder, and partial or total remission. Treatment also includes prolonging survival as compared to expected survival if not receiving treatment. The methods of the invention are particularly appropriate for the prevention of events traditionally associated with COPD, or for treating a pre-existing condition, including for example decreasing outpatient exacerbations and hospitalizations, decreasing inhalant use, decreasing sputum production, or of dyspnea. Notably, the methods of the invention are useful to reduce the and the frequency of acute steroid treatment and the average steroid dose used for COPD patients. The latter includes foremost COPD patients that have become steroid dependent (Omalizumab treated patients reduced steroid use by 50%, data not shown). Remarkably, the present methods have also been found to reduce the frequency of antibiotic treatment traditionally used for the management of COPD The term "therapeutically effective amount" is used to denote treatments at dosages effective to achieve the therapeutic result sought. Furthermore, one of skill will appreciate that the therapeutically effective amount of the compound of the invention may be lowered or increased by fine tuning and/or by administering more than one anti-IgE moiety according to the invention, or by administering a moiety of the invention with another COPD therapeutic moiety known in the art.

Generally, the "therapeutic amount" of a substance or composition depends upon the context in which it is being applied. In the context of administering a composition that inhibits IgE activity, a therapeutic amount is an amount sufficient to achieve any such inhibition. One of skill in the art will appreciate that inhibition need not be complete.

Further, as would be readily understood by one skilled in the art, the active ingredients described in any of the embodiments herein may be combined into a single composition for simultaneous administration of one or more of the active ingredients. Similarly, anti-IgE moieties according to the invention may be administered in conjunction with other therapeutic modalities such as those traditionally used for the treatment of COPD (e.g., bronchodilators such as for example formoterol or salmeterol, antibiotics, oxygen therapy, corticosteroids, mediator antagonists, protease inhibitors, and various anti-inflammatory) (for example, see P. J. Barnes, New Engl. Journ. Med. 343:269-279 (2000) and Sutherland, E. R., Cherniack, R. M. *New Engl. J. Med.* 350:2689-2697 (2004); and Sutherland, E. R., Allmers, H., Ayas, N. T., Venn, A. J., Martin, R. J. *Thorax* 58:937-941 (2003)). For example, in addition to the regular, periodic administration of Omalizumab, management of patients may include the use of antibiotics and/or steroids during acute exacerbation, as well as expectorants, mucolytics, inhalation treatments, leukotriene modifiers, and amonophylics preparations, when indicated. In certain instances, the therapeutic methods of the invention may be further augmented by careful consideration and evaluation of risk factors in the home and workplace.

The invention therefore provides in certain aspects methods to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect. Moreover, it will be appreciated that the amount of a moiety of the invention required for use in treatment will vary with the nature of the condition being treated and the age and the condition of the patient and will be ultimately at the discretion of the attendant physician or veterinarian. In general, however, doses employed for human treatment will typically be as described for Omalizumab (see specifics of dosage and administration for XOLAIR® (Omalizumab) at http://www.gene.com/gene/products/information/immunological/xolair/insert.jsp). The desired dose may conveniently be presented in a single dose or as divided doses administered at appropriate intervals, for example as two, three, four or more sub-doses per day. It will be appreciated by those of skill in the art that the number of administrations of the anti-IgE moieties according to the invention will vary from patient to patient based on the particular medical status of that patient at any given time including other clinical factors such as age, weight and condition of the mammal and the route of administration chosen.

The effective dosage for Omalizumab for the treatment of asthma has been found to be from 150 to 375 mg administered SC every 2 or 4 weeks. Doses (mg) and dosing frequency are determined by serum total IgE level (IU/mL), measured before the start of treatment, and body weight (kg). In certain instances, it has been observed that the therapeutically effective time window for the administration of Omalizumab in COPD may be extended beyond the four weeks recommended for Omalizumab for the treatment of asthma. In certain instances COPD patients have been found to respond to Omalizumab administrations spaced as many as six weeks apart. Similarly, it has been found that the therapeutically effective dosage of Omlizumab for the treatment of COPD may be reduced by half as compared to the dosage recommended for the treatment of asthma. For five patients who were stabilized on the recommended dosage schedule, the frequency of treatments could be reduced. Three patients on a 4 week schedule were decreased to a 6 week schedule, and 2 patients on a 2 week schedule were decreased to a 4 week schedule. These 5 patients have remained stable on these reduced treatment schedules.

As used herein, "therapeutically effective time window" means the time interval wherein administration of the compounds of the invention to the subject in need thereof reduces or eliminates the deleterious effects or symptoms.

The methods of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses. In certain instances the invention is described in reference to subjects or patients. Such terms are used interchangeably and designate any mammal that may experience the benefits of the methods of the invention.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art.

Standard reference works setting forth the general principles of pharmacology include Goodman and Gilman's *The Pharmacological Basis of Therapeutics*, 10th Ed., McGraw Hill Companies Inc., New York (2001). Standard references setting forth general principles of internal medicine include *Harrison's Principles of Internal Medicine*, 12th Edition, Wilson, et al., eds., McGraw-Hill, Inc.

As used in this specification, the singular forms "a", and "the" specifically also encompass the plural forms of the terms to which they refer, unless the content clearly dictates otherwise.

As used herein, unless specifically indicated otherwise, the word or is used in the "inclusive" sense of "and/or" and not the "exclusive" sense of "either/or."

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process or method, the term "comprising" means that the process/method includes at least the recited steps, but may include additional steps.

Any suitable materials and/or methods known to those of skill can be utilized in carrying out the present invention. However, preferred materials and methods are described. Materials, reagents and the like to which reference is made in the following description and examples are obtainable from commercial sources, unless otherwise noted.

The moieties useful according to the methods of the invention are optionally formulated in a pharmaceutically acceptable vehicle with any of the well known pharmaceutically acceptable carriers, including diluents and excipients (see *Remington's Pharmaceutical Sciences*, 18th Ed., Gennaro, Mack Publishing Co., Easton, Pa. 1990 and *Remington: The Science and Practice of Pharmacy*, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of moieties according to the invention may contain more than one type of compound of the invention), as well any other pharmacologically active ingredient useful for the treatment of the symptom/condition being treated.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLE I

Selection Criteria for Inclusion in the Evaluation Study

Testing of the usefulness of anti-IgE for the treatment of COPD was carried on 143 patients with symptoms requiring ongoing management. For each patient, age, sex, smoking history, and family history (15' degree relatives) of allergic or obstructive disease were recorded. Serum IgE was measured in International Units (IU). Serum eosinophil levels were measured in most cases. Atopy was evaluated with skin test reactivity to a panel of 24 relevant inhalant antigens according to guidelines of the American Academy of Allergy, and was scored on a severity scale of 0 to 3 (3=prick test reactivity with wheal≥2 mm; 2=prick test reactivity with wheal≤2 mm; 1=negative prick test reactivity with intradermal reactivity only; 0=no reactivity). The individual skin test scores were added to obtain a total skin test score. Pulmonary function tests (PFT) were performed on a Collins G. S. Spirometer according to American Thoracic Society guidelines; reversibility was defined as an increase of 20% or greater in the forced expiratory volume in the first second (FEV1) after bronchodilator treatment.

A Registered Nurse administered Omalizumab by subcutaneous injection in a clinic held every 2 weeks. The dose, in milligrams, and its frequently of administration were given according to the recommendations for XOLAIR (see package labeling provided by Genentech Corporation, South San Francisco, Calif.). An interim history and focused physical exam were performed at each clinical visit. The baseline period was the 12-month period before the first Omalizumab injection. The treatment period began two months after the initial injection.

Patients were selected for Omalizumab treatment on the basis of severity of disease as manifested by one or more exacerbations in the baseline year requiring hospitalization, emergency room visit, or office visit; and also a COPD severity score of ≥11 (see Eisner M., Trupin L., Katz P. *Chest* 2005; 127:1890-1897).

The primary end point of the study was a reduction in the number of acute exacerbations resulting in hospitalizations or in outpatient visits. Each patient served as his/her own control. Exacerbations were binned in 2 month intervals. The average exacerbation rate for each 2 month interval was computed by dividing the total number of exacerbations in that interval by the number of patients evaluated in that 2 month time interval. The exacerbation rates for each patient in the baseline period and in the first year of treatment were analyzed by Wilcoxon signed-ranked test. The average exacerbation rates for the group as a whole in the baseline year and in the first and second treatment years were analyzed by Student t-tests. Statistical analysis was performed with the STATA package (STATA Corp, College Station, Tex., USA). Correlation analyses were performed both with the correlation coefficient r, and with linear regression analysis and associated p value.

EXAMPLE II

Evaluation Study

Patients Demographics

The demographics of the 143 patients evaluated are presented in Table 1.

TABLE 1

Patients with symptoms requiring ongoing management (Group 1-4) from which 17 patients were selected to receive Omalizumab.

| | Patient Groups N = 143 | | | |
|---|---|---|---|---|
| | 1 | 2 | 3 | 4 |
| | $IgE \geq 30$ IU | | $IgE < 30$ IU | |
| | Smoker | Non-smoker | Smoker | Non-Smoker |
| Number | 68 | 20 | 39 | 16 |
| Age range (median) | 30-80 (65) | 17-85 (53) | 35-83 (65) | 39-84 (73) |
| Female | 21 | 12 | 27 | 13 |
| Family history of obstructive disease | 45 | 17 | 25 | 5 |
| IgE (IU) (median) | 32-1618 (110) | 31-858 (140) | 0-22 (7) | 0-25 (6) |
| Positive skin tests | 41/49 | 18/20* | 6/12 | 4/10 |
| Eosinophilia (>300) | 27/62 | 12/19 | 7/34 | 4/15 |
| Reversibility ($\geq 15\%$) | 11 | 5 | 4 | 0 |
| Baseline $\geq 80$ | 16 | 12 | 5 | 7 |
| FEV1 (% 50-80 | 39 | 6 | 16 | 9 |
| predicted) <50 | 13 | 2 | 18 | 0 |

*One additional patient in this group who was not skin tested had positive RAST panel.

There were 110 patients (72%) with a primary cigarette history (Groups 1+3), indicating a large proportion of patients with a cigarette history in this practice.

There were 88 patients (62%) with an $IgE \geq 30$ IU (Groups 1+2), indicating a large proportion of patients with a measurable IgE level. Of these patients, 68 (77%) had a primary cigarette history exposure (Group 1). A family history of obstructive disease was present in 62 patients (70%). Sixty-nine patients underwent allergy testing. In 59 patients skin tests were positive, and in 1 further patient a regional allergy serum test (RAST) was positive, giving a total of 60 positive allergy studies (87% of those evaluated); 9 patients (13%) of the 69 allergy tested patients were non-responders. An elevated peripheral eosinophil count was present in 39 of 81 patients evaluated (48%).

EXAMPLE III

Evaluation Study

Omalizumab Treatment Group

Of the 88 patients in with an $IgE \geq 30$ IU, 17 were entered into the study (Table 2) on the basis of disease severity in the one year baseline period prior to treatment—16 patients had experienced a total of 60 acute exacerbations that resulted in 20 hospitalizations and 40 outpatient emergency room/doctor visits, while 1 patient was Oz and steroid dependant with 3 prior intubations (four patients, overall, were $O_2$ dependant). They had severe obstructive disease—8 patients had an FEV1 of less than 50% predicted. There was minimal reversibility—5 patients of the 16 had reversibility$\geq 15\%$. The COPD severity score ranged from 11 to 28. Eight patients had positive skin tests to both indoor and outdoor allergens, 6 patients were positive to indoor allergens alone, and 2 patients were negative to skin testing as well as to RAST testing (Table 3).

TABLE 3

Skin test reactivity to inhaled allergens

| INHALED ALLERGEN | NUMBER OF PATIENTS TESTING POSITIVE | AVERAGE REACTIVITY SCORE |
|---|---|---|
| Dust mites | 14 | 2.1 |
| Cat dander | 9 | 2.8 |
| Grasses | 7 | 2.9 |
| Molds | 5 | 1.6 |
| Dog dander | 2 | 2.5 |
| Tree pollen | 2 | 2.5 |
| Cockroach | 1 | 3.0 |

Thirteen patients had a heavy cigarette smoking history, in most cases of several decades duration; 4 patients had only a secondary cigarette exposure. All 17 patients were on inhaled or oral steroids, 13 were on a leukotriene receptor antagonist, 12 were on a long acting beta agonist, 4 were on oral theophylline. (Patients not on a leukotriene receptor antagonist or long-acting beta agonist had not responded to these therapies previously.)

Of the 71 patients with an $IgE \geq 30$ IU not treated with Omalizumab, 59 patients had relatively mild disease with no hospitalizations in the previous year and COPD severity scores$\leq 10$. There were 12 patients with severe disease who were not treated—3 had IgE levels>1000 IU, 3 had other comorbid severe illnesses, 2 moved out of the area, and 4 deferred treatment.

EXAMPLE IV

Evaluation Study

Findings

Figure 1A:
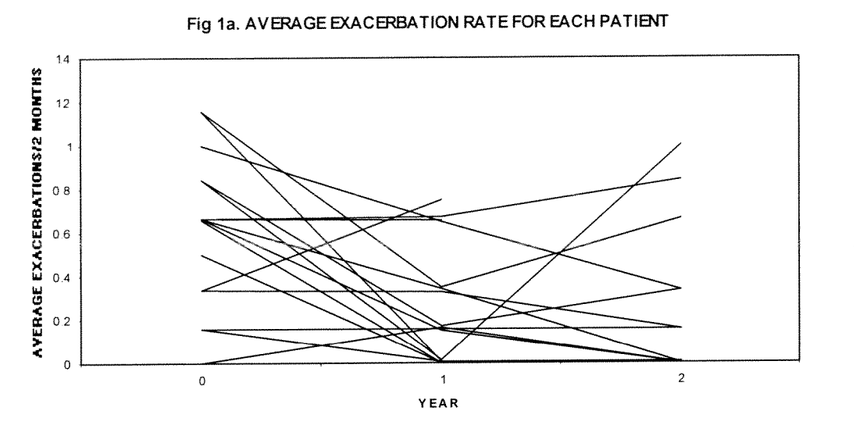
FIG. 1a: Exacerbation rate for each of the 17 patients in the baseline year and treatment years 1 and 2.

As of May 1, 2006, 9 patients are in their third year of Omalizumab treatment, 6 patients are in their second year of Omalizumab treatment, and 2 patients have completed 10 months of treatment. Twelve patients of the 17 showed a decrease in exacerbation rates from baseline year to the first treatment year, 3 patients had no change, and 2 patients had an increased rate, (p<0.01 by Wilcoxon signed-rank test, Table 4, FIG. 1a).

TABLE 4

Response to Omalizumab treatment

4a. Change in exacerbations from baseline year to first year of treatment

|  | Number of patients |
| --- | --- |
| Decreased exacerbations | 12 |
| No change | 3 |
| Increased exacerbations | 2 |

4b. Average exacerbations per patient per 2-month interval (Mean ± standard deviation)

|  |  | Comparison with baseline year |
| --- | --- | --- |
| Baseline year | .61 ± .16 |  |
| Treatment year 1 | .25 ± .02 | p < .01 |
| Treatment year 2 | .26 ± .15 | P < .01 | p < .01 Wilcoxon signed rank test
p < .01 Student t-test

Figure 1B:
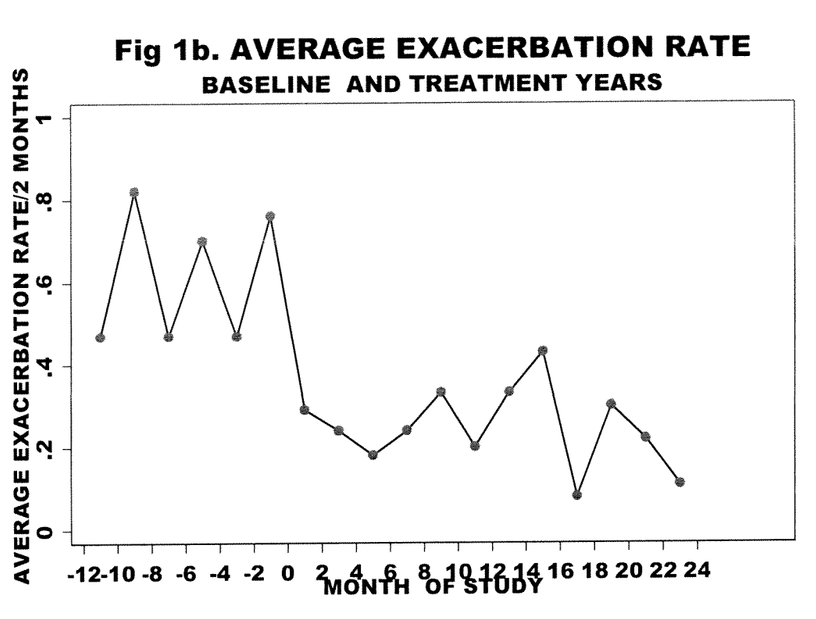
FIG. 1b: Average exacerbation rate in 2 month intervals for the 17 treated patients during the baseline year (months—12 to 0) and treatment years (months 0 to 24).
Figure 1C:
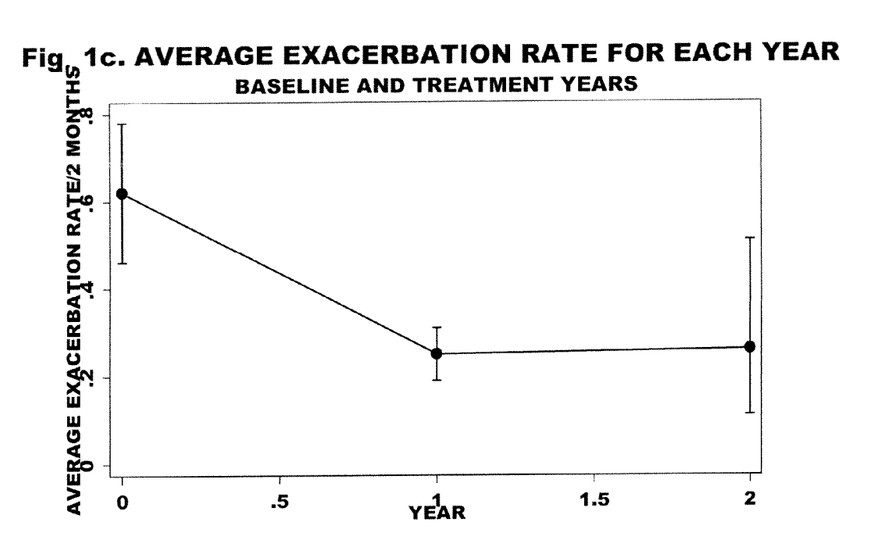
FIG. 1c: Average exacerbation rate in the baseline year and in years 1 and 2.

The average exacerbation rates (in each 2 month interval) declined consistently between the baseline year and the treatment years (FIG. 1b). The overall average exacerbation rate for the 17 patients as a whole declined from 0.61±0.15 in the baseline year to 0.25±0.02 in the first year of treatment, and 0.26±0.15 in the second year after treatment (p<0.01 by paired Student t-test, Table 4, FIG. 1c).

The response rate to Omalizumab treatment was analyzed in terms of several constituent variables. Statistical analysis included correlation coefficients, linear regression analysis, and graphical regression fits.

Figure 2A:
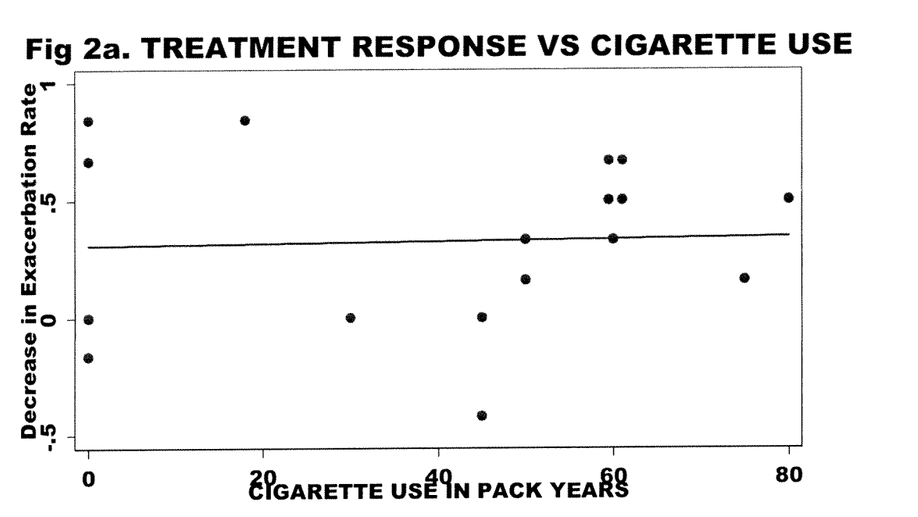
FIG. 2a shows cigarette exposure in pack years. Patients with secondary exposure alone were assigned zero.

Cigarettes: There was no correlation between the number of pack years of cigarette use and the response rate of exacerbations to Omalizumab treatment (Table 6, r=0.04, p=0.7). The regression line fit was essentially flat, with a wide scatter outside the 95% confidence interval (FIG. 2a). Patients with a heavy cigarette exposure were as likely to respond to Omalizumab as patients with a modest primary exposure or secondary exposure.

Figure 2B:
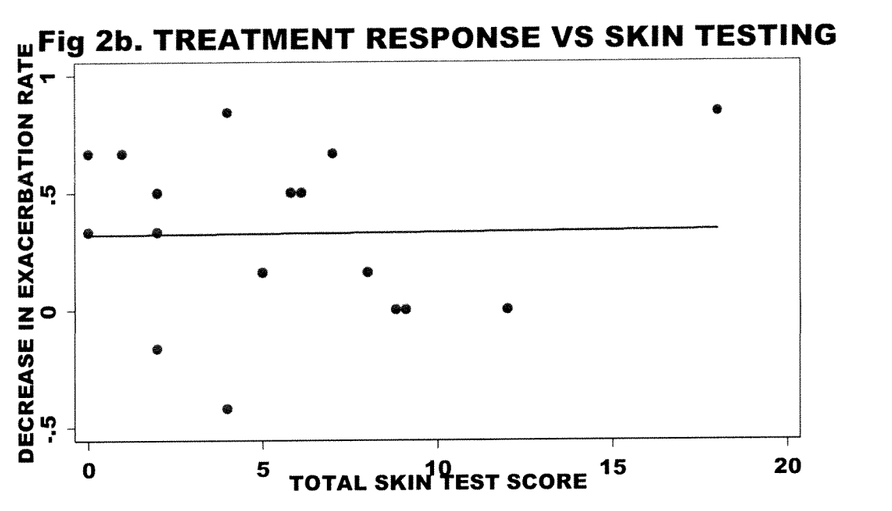
FIG. 2b shows the Total skin test score=sum of individual skin test reactions for each patient.

IgE: While the presence of an IgE-mediated allergic response at the tissue level is the sine qua non for anti-IgE therapy, the level of circulating IgE was not a predictor of the degree of response (r=0.25, p=0.3, Table 5, FIG. 2b).

TABLE 5

Correlation analysis and regression analysis of response rate change (Deltaexac) with patient characteristics

| Variable (x) | r correlation coefficient | Deltaexac = a * x + b | | |
| --- | --- | --- | --- | --- |
|  |  | a | b | p |
| Cigarette use (pack years) | −.04 | −.001 | −.264 | .7 |
| IgE (IU) | +.25 | .0006 | −.400 | .3 |
| Total score of skin test Reactivities | +.01 | +.001 | −.322 | .9 |

TABLE 5-continued

Correlation analysis and regression analysis of response rate change (Deltaexac) with patient characteristics

| Variable (x) | r correlation coefficient | Deltaexac = a * x + b | | |
| --- | --- | --- | --- | --- |
|  |  | a | b | p |
| FEV1 (% predicted) | +.11 | −.002 | −.201 | .7 |
| % Change in FEV1 post-bronchodilator | −.19 | .009 | −.394 | .4 |

Figure 2C:
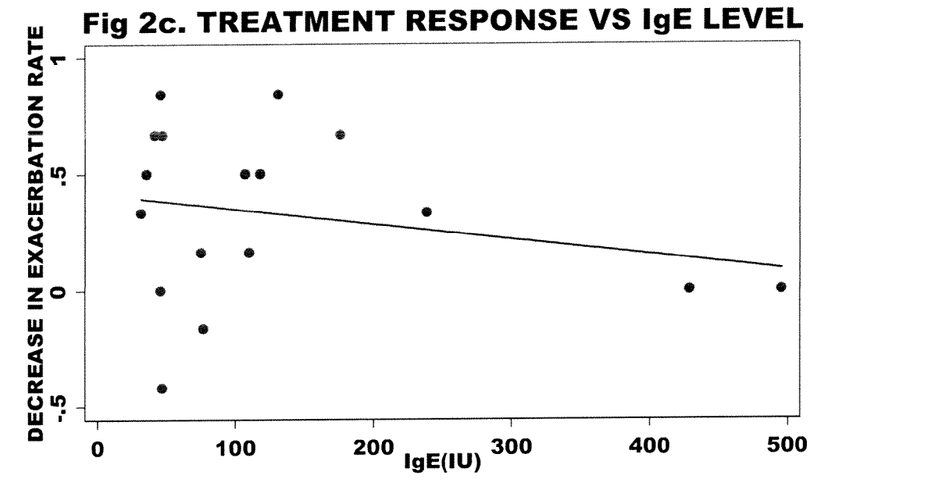
FIG. 2c. is a graph showing the IgE (IU)=serum IgE level in IU in the patients tested.

Skin test reactivity: For each of the 17 patients, the total sum of their individual skin test scores was added, and then regressed to the response with Omalizumab treatment. The correlation coefficient (r=0.01), the regression fit (p=0.9), and the regression scatter diagram all suggest an absence of a strong correlation (Table 5, FIG. 2c). Patients who were skin-test negative or weakly positive (skin test scores≤2) had response rates to Omalizumab similar to those patients who were more strongly skin test positive.

FEV1: While a reversible FEV1 is often characteristic of the allergic asthmatic, most of the patients in our population had severe fixed airway disease—only 5 demonstrated reversibility≥15%, and 9 had an FEV1<50% predicted. The goal of Omalizumab treatment in this patient group would not, therefore, be an improvement in resting FEV1 in a quiet PFT lab setting, but a prevention of subsequent IgE-mediated exacerbations as measured by hospital or outpatient visits. The response rate to Omalizumab was regressed against FEV1% and also against the degree of reversibility of FEV1% with bronchodilator treatment. Neither of these correlations was significant (Table 5).

What is claimed is:

1. A method of treating a mammal having COPD consisting essentially of administering a therapeutically effective amount of an anti-immunoglobulin E (IgE) antibody to the mammal; wherein the anti-IgE antibody reduces or blocks the binding of soluble IgE to its receptors, and wherein the administration results in an outcome comprising a reduction in the number of acute exacerbations experienced by the mammal.

2. The method according to claim 1, wherein the anti-IgE antibody is a humanized IgG antibody that selectively binds to human IgE.

3. The method according to claim 2, wherein the humanized IgG antibody that selectively binds to human immunoglobulin E is a monoclonal antibody.

4. The method according to claim 1, wherein the anti-IgE antibody is omalizumab.

5. The method according to claim 1, wherein the mammal has an elevated serum IgE level.

6. The method according to claim 1, wherein the mammal has a negative skin test to an inhalant antigen.

7. The method according to claim 1, wherein the mammal has a negative in vitro reactivity to a perennial aeroallergen.

* * * * *